United States Patent [19]

Bohlmann et al.

[11] Patent Number: 5,135,937
[45] Date of Patent: Aug. 4, 1992

[54] CYCLOALKYLENE AZOLES AND PHARMACEUTICAL PREPARATIONS OBTAINED THEREFROM

[75] Inventors: Rolf Bohlmann; Peter Strehlke; David Henderson; Martin Schneider; Yukishige Nishino, all of Berlin, Fed. Rep. of Germany

[73] Assignee: Schering Aktiengesellschaft, Berlin and Bergkamen, Fed. Rep. of Germany

[21] Appl. No.: 563,114

[22] Filed: Aug. 3, 1990

[30] Foreign Application Priority Data

Aug. 4, 1989 [DE] Fed. Rep. of Germany ....... 3926365

[51] Int. Cl.$^5$ .................... A61K 31/41; C07D 249/04
[52] U.S. Cl. ...................................... 514/359; 548/255
[58] Field of Search ......................... 548/255; 514/359

[56] References Cited

U.S. PATENT DOCUMENTS 4,609,666 9/1986 Hirsch et al. ...................... 548/255

FOREIGN PATENT DOCUMENTS 0227100 7/1987 European Pat. Off. .
0236940 9/1987 European Pat. Off. .

Primary Examiner—Patricia L. Morris
Attorney, Agent, or Firm—Millen, White & Zeiano

[57] ABSTRACT

The disclosure relates to cycloalkylene azoles of general Formula I

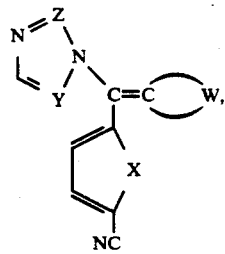

wherein

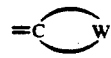

is a carbocyclic or carbopolycyclic group optionally carrying at least one alkyl substituent,
X is the grouping

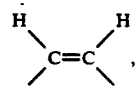

an oxygen or sulfur atom, and
Y and Z, independently of each other, are

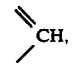

or a nitrogen atom,
as well as their pharmaceutically compatible addition salts with acids as well as processes for production thereof. The compounds possess strongly aromatase-inhibiting activity and are suitable for the preparation of medicinal agents.

Methods for treating estrogen induced or stimulated tumors, male infertility, and impending cardiac infarction with these compounds are also provided as well as methods for inhibiting female fertility.

15 Claims, No Drawings

CYCLOALKYLENE AZOLES AND PHARMACEUTICAL PREPARATIONS OBTAINED THEREFROM

SUMMARY OF THE INVENTION

The invention relates to cycloalkylene azoles of the general Formula I

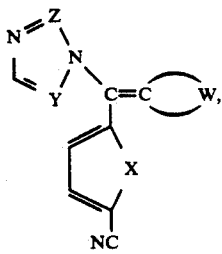
(I)

wherein

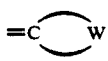

is a carbocyclic or carbopolycyclic group optionally carrying one or more alkyl substituents,

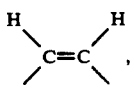

X is the grouping
an oxygen or sulfur atom, and
Y and Z, independently of each other, are a methyne group,

or a nitrogen atom, as well as their pharmaceutically compatible salts with acids, to a process for the production of the cycloalkylene azoles of general Formula I, to pharmaceutical preparations containing these cycloalkylene azoles, as well as their use AS medicinal agents.

Carbopolycyclic includes aliphatic groups having one to three rings (fused or linked by a covalent bond) each of three to seven carbon atoms, 7 to 20 carbon atoms in total.

The carbocyclic or carbopolycyclic group,

herein is preferably a cycloalkylidene group of 4 to 20, most preferably 4 to 10, carbon atoms. The cycloalkylidene groups are preferably cyclopentylidene, cyclohexylidene, cycloheptylidene or adamantylidene groups. Also suitable with preference are cyclobutylidene, cyclooctylidene, cyclononylidene and, cyclodecylidene groups and the polycycloalkylidene groups bicycl[3.3.1]non-9-ylidene and spiro[5.5]undec-3-ylidene.

The polycycloalkylidene groups preferably have from 7 to 20 carbon atoms.

If the carbocyclic or carbopolycyclic group,

carries alkyl substituents, these are preferably several straight-chain or branched $C_{1-6}$-alkyl residues, most preferably 1 to 4 straight-chain or branched $C_{1-4}$-alkyl alkyl residues.

Preferably, X is the grouping

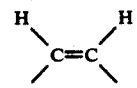

or a sulfur atom, and preferably Y and Z are selected so that the group

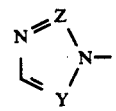

is a 1-imidazolyl, 1,2,3-triazolyl or 1,2,4-triazolyl ring.

Examples of pharmaceutically compatible salts of the cycloalkylene azoles of general Formula I include those obtained with malonic acid, succinic acid, with hydrogen chloride and hydrogen bromide.

The compounds set forth below, and the pharmaceutically compatible salts thereof, are especially preferred according to this invention:
4-[1-cyclohexylidene-1-(imidazolyl)methyl]benzonitrile, hydrochloride;
4-[1-cyclopentylidene-1-(imidazolyl)methyl]benzonitrile;
4-[1-cycloheptylidene-1-(imidazolyl)methyl]benzonitrile;
4-[2-adamantylidene-1-(imidazolyl)methyl]benzonitrile;
4-[1-cyclohexylidene-1-(1,2,4-triazolyl)methyl]benzonitrile;
4-[1-cyclopentylidene-1-(1,2,4-triazolyl)methyl]benzonitrile;
4-[1-cycloheptylidene-1-(1,2,4-triazolyl)methyl]benzonitrile;
4-[2-adamantylidene-1-(1,2,4-triazolyl)methyl]benzonitrile;
4-[1-cyclohexylidene-1-(1,2,3-triazolyl)methyl]benzonitrile;
4-[1-cyclopentylidene-1-(1,2,3-triazolyl)methyl]benzonitrile;
5-(cyclohexylidene-1-imidazolylmethyl)thiophene-2carbonitrile;
4-[1-(3,3,5,5-tetramethyl-1-cyclohexylidene)-1-(1-imidazolyl)methyl]benzonitrile;
4-[1-cycloheptylidene-1-(1,2,3-triazol-1-yl)methyl]benzonitrile;
4-[1-cyclodecylidene-1-(1-imidazolyl)methyl]benzonitrile;
4-[1-cycloheptylidene-1-(1-imidazolyl)methyl]benzonitrile,hydrochloride;
4-[1-(4-tert-butyl-1-cyclohexylidene)-1-(1-imidazolyl)methyl]benzonitrile;

4-[1-(3,4-dimethyl-1-cyclopentylidene)-1-(1-imidazolyl)methyl]benzonitrile; (mixture of isomers cis/trans);

4-[1-(3,5-dimethyl-1-cyclohexylidene)-1-(1-imidazolyl)-methyl]benzonitrile;

4-[1-(4-methyl-1-cyclohexylidene)-1-(1-imidazolyl)methyl]benzonitrile;

4-[1-cyclononylidene 1-(1-imidazolyl)methyl]benzonitrile;

4-[1-(bicyclo[3.3.1]non-9-ylidene)-1-(1-imidazolyl)methyl]benzonitrile;

4-[1-(1-imidazolyl)-1-(spiro[5.5]undec-3-ylidene)methyl]benzonitrile;

4-[1-cyclooctylidene 1-(1-imidazolyl)methyl]benzonitrile;

4-[1-(2,6-dimethyl-1-cyclohexylidene)-1-(1-imidazolyl)-methyl]benzonitrile;

4-[1-cyclohexylidene-1-(1-imidazolyl)methyl]benzonitrile;

4-[1-(2-adamantylidene)-1-(1,2,3-triazol-1-yl)methyl]-benzonitrile;

4-[1-(2-adamantylidene)-1-(1,2,4-triazol-1-yl)methyl]-benzonitrile;

4-[1-(2-adamantylidene)1-(1-imidazolyl)methyl]benzonitrile, hydrochloride;

4-[1-cyclobutylidene .1-(1-imidazolyl)methyl]benzonitrile;

5-[cyclopentylidene-(1-imidazolyl)methyl]thiophene2-carbonitrile.

The compounds of general Formula I and pharmaceutically compatible salts thereof are inhibitors of estrogen biosynthesis (aromatase inhibitors). They are consequently suited for the treatment of diseases caused by estrogens or dependent on estrogens. Thus, they are suitable for the treatment of estrogen-induced or -stimulated tumors, e.g., mamma carcinoma or hyperplasia of the prostate (The Lancet, 1984:1237-1239). A preferred dosage range for this treatment is 0.001 to 1.0, most preferably 0.01 to 0.1, mg/kg body weight/day. The effectiveness of the compounds of the present invention for treatment of estrogen-induced or stimulated tumors can be routinely demonstrated by the methods of Scheides et al. in *Europ. J. of Cancer and Clinical Oncol.,* Vol. 25, No. 4, pp. 691-701. The compounds of this invention can be administered for such treatments analogous to the aromatase inhibitor aminoglutethimide.

The compounds of this invention are also valuable for affecting fertility. Thus, male infertility resulting from increased estrogen levels can be overcome by means of the novel active compounds. A suitable dosage range for this treatment is 0.0001 to !0 mg/kg body weight/day. Furthermore, the compounds can be utilized as anti-fertility agents in women of childbearing age in order to inhibit ovulations by estrogen withdrawal. A suitable dosage range for this treatment is also 0.0001 to 10 mg/kg body weight/day.

Aromatase inhibitors are probably also suited for treatment of impending cardiac infarction since elevated estrogen levels in males can precede cardiac infarction (U.S. Pat. No. 4,289,762). A suitable dosage range for this treatment is expected to be 0.0001 to 10 mg/kg body weight/day.

The compounds of this invention can be administered analogous to the aromatic inhibitor aminoglutethimide in treating diseases or conditions dependent on estrogens.

Known compounds exhibiting aromatase-inhibiting activity are, besides steroids, also non-steroidal substances, for example the diverse nitrogen heterocycles described in European Patent Applications EP-A 0165777 through 0165784; the substituted glutaric acid imides described in J. Med. Chem. 1986, 29: 1362-1369; the substituted imidazobenzenes disclosed in European Patent Application EP-A 0165904; the heterocyclic-substituted toluene nitriles set forth in European Patent Application EP-A 0236940; as well as the imidazo- and 5,6,7,8-tetra-hydroimidazol[1,5a]-pyridines carrying an optionally substituted phenyl ring disclosed in U.S. Pat. No. 4,728,465, among which 5-(p-cyanophenyl)-5,6,7,8-tetrahydroimidazol[1,5a]-pyridine, hydrochloride excels, in particular, as a strongly effective aromatase inhibitor (Cancer Res., 48 : 834-838, 1988).

The compounds of the present application are distinguished with respect to the previously known compounds in that they inhibit the enzyme system of aromatase more vigorously and, at the same time, more selectively. The selective action can be seen from the fact that other enzyme systems are impaired to a lesser extent. The compounds of the present application are furthermore distinguished in that they are not chiral and therefore cannot occur as a 1:1 mixture of the differently effective antipodes.

The aromatase-inhibiting activity of the compounds according to the invention can be demonstrated in vitro (test a), as well as in vivo (test b). The following compounds are examined as representative:

Test (a)

4-[1-Cyclohexylidene-1-(1-imidazolyl)methyl]benzonitrile, hydrochloride (A);

4-[1-Cyclohexylidene-1-(1-imidazolyl)methyl]benzonitrile (B).

Test (b)

Compound A,
Compound B,
4-[1-Cyclopentylidene-1-(1-imidazolyl)methyl]benzonitrile (C).

The comparison compound used in both tests is the aromatase inhibitor 5-(p-cyanophenyl)-5,6,7,8tetrahydroimidazo[-1,5a]pyridine, hydrochloride, known from U.S. Pat. No. 4,728,645, in the form of the racemate (D).

Description of Test (a)

Aromatase Inhibition in Human Placenta

The abilities of the compounds of inhibiting the enzyme system of aromatase is tested on microsomes obtained from human placenta. In accordance with the method by Thompson and Siiteri (J. Biol. Chem., 249 : 5364-72 [1974]) the release of tritium-labeled water ($^3H_2O$), liberated as the reaction product in the aromatization of [$1\beta$-$^3H$]-androstenedione to the estrone, is measured. The corresponding inhibition values ($K_i$, aromatase) are determined by graphic means, plotting $1/v$ against the inhibitory concentration in accordance with the method by Dixon (Biochem. J., 94 : 760 [1965]).

| Compound | $K_i$, Aromatase |
|---|---|
| 4-OH-Androstenedione (*) | 62.0 nmol/l |
| A | 0.19 nmol/l |
| D | 1.2 nmol/l |
| 4-OH-Androstenedione | 41.0 nmol/l |

-continued

| Compound | $K_i$, Aromatase |
|---|---|
| (*) B | 0.48 nmol/l |

(*) as the reference compound

Description of Test (b)
Influence on Androstenedione-Induced Uterus Growth in Infantile Rats Infantile female rats receive once daily the compound to be tested in combination with androstenedione over a period of three days. One group receives only androstenedione, and a further group only the vehicle. One day after the last treatment, the animals are sacrificed by decapitation and exsanguination, and the fresh uterus weights (without content) are determined. The uterus weights are calculated for mg/100 g body weight. The average value and standard deviation are calculated for each group. Variance analysis is used to check the significances of the differences with respect to the control group (androstenedione group and, respectively, vehicle group). Furthermore, the percentage inhibition of uterus growth is determined, based on the androstenedione group. In this determination, the uterus weight of the vehicle group (basic value) is deducted from the corresponding weight of the androstenedione group. The individual dosage groups, after subtracting the basic value, are based on the thus-obtained value.

| Compound | Dosage mg/kg/Day | Uterus Weight mg/100 g BW* | Inhibition in % |
|---|---|---|---|
| Control | Vehicle** | 61.0 ± 16.1 | |
| Androstenedione (AD) | 30 | 213.6 ± 32.4 | |
| A + AD | 2.0 + 30 | 100.1 ± 18.8 | 74 |
| A + AD | 0.2 + 30 | 108.2 ± 11.9 | 69 |
| D + AD | 0.2 + 30 | 83.2 ± 6.9 | 86 |
| Control | Vehicle | 48.8 ± 5.0 | |
| Androstenedione (AD) | 30 | 183.5 ± 22.7 | |
| B + AD | 2.0 + 30 | 72.5 ± 10.3 | 82 |
| C + AD | 2.0 + 30 | 69.2 ± 5.7 | 85 |
| D + AD | 0.2 + 30 | 69.9 ± 6.6 | 84 |

*BW = Body Weight
**"Myrj" + phys. Sodium Chloride Solution (1:1)

In comparison with the compounds of EP-A 0236940, the compounds of general Formula I according to this invention no longer have a center of chirality, on account of the introduction of the double bond, on the carbon atom carrying the cyanoaryl as well as the N-heteroaryl residue. Owing to the elimination of the chirality center, problems are avoided in the processing and separation of stereoisomeric compounds.

The amount of compounds to be administered varies within a wide range and can cover any effective quantity. In dependence on the condition to be treated and the form of administration, the amount of compounds administered can be 0.0001-10 mg/kg of body weight, preferably 0.001-1 mg/kg of body weight per day, most preferably 0.01 to 0.1 mg/kg of body weight per day.

Suitable for oral administration are capsules, pills, tablets, dragees, etc. The dosage units can contain, beside the active ingredient, a pharmaceutically compatible vehicle, e.g., amylose, sugar, sorbitol, gelatin, lubricants, silicic acid, talc, etc. Suitable pharmaceutically compatible vehicles also include those described in U.S. Pat. No. 4,728,645. The individual dosage units for oral administration can contain, for example, 0.05-50 mg of the active agent (the aromatase inhibitor).

For parenteral administration, the active compounds can be dissolved or suspended in a physiologically compatible diluent in an amount of 0.1 to 10% by weight. With frequency, the diluents employed are oils with or without the addition of a solubilizer, of a surfactant, of a suspension mixture or of an emulsifying mixture. Examples of oils utilized that can be cited are: olive oil, peanut oil, cottonseed oil, soybean oil, castor oil, and sesame oil.

The compounds can also be used in the form of a depot injection or of an implant preparation which can be formulated so that sustained release of active agent is made possible.

Implants can contain, as inert materials, for example biodegradable polymers or synthetic silicones, such as, for example, silicone rubber. The active ingredients can furthermore be incorporated into plasters, for example, for percutaneous application.

The invention accordingly also relates to pharmaceutical preparations which comprise a cycloalkylene azole of general Formula I, or a pharmaceutically compatible salt thereof with acid, and a pharmaceutically compatible vehicle. The invention also relates to methods for inhibiting aromatase activity, including treatments of tumors induced or stimulated by estrogen, treatments of male infertility, methods of birth control through inhibition of female fertility and treatments of impending cardiac infarction.

The invention furthermore concerns processes for the production of cycloalkylene azoles of general Formula I.

In the first process, a compound of general Formula II

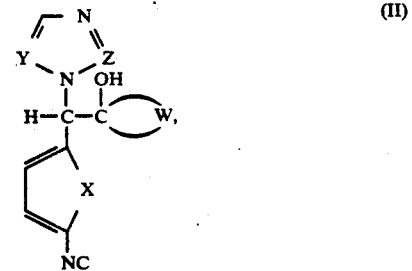

(II)

wherein

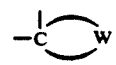

is a carbocyclic or carbopolycyclic group and
X, Y and Z have the meanings indicated in Formula I, is converted to a compound of general Formula I by splitting off HOH either by heating or by the addition of base, with or without additional heating. Optionally, the hydroxy group can be transformed to another group or radical, A, and treatments with heat, base or both will split off HA.

In a second method, a dihalogenide of general Formula III

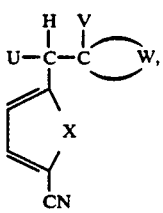

wherein

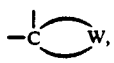

X, Y and Z have the meanings given in Formulas I and II, and

U and V are halogen atoms which can be identical or different, preferably 2 bromine atoms, is converted, by reaction with a heterocycle of general Formula IV

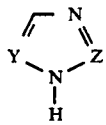

wherein

Y and Z have the meanings indicated in Formula I, into a compound of general Formula I, which is optionally converted, by reaction with an acid, into a pharmaceutically compatible salt. The use of an auxiliary base during the conversion of the dihalogenide of general formula III is optional.

In the first process, the hydroxy group, prior to introduction of the double bond, is preferably transformed to a chlorine function by reacting the hydroxy compound, for example, with thionyl chloride. The subsequent splitting off of hydrogen chloride can then be brought about in a simple way by further heating in the chlorinating agent. However, in general, it is expedient to effect introduction of the double bond by splitting off HOH or HA under the effect of a base. A suitable base, inter alia, is, for example, moderately concentrated aqueous sodium hydroxide solution or triethylamine.

In the second version, the reaction of a compound of Formula III with a compound of Formula IV takes place with or without a solvent; in the latter case, the temperature ranges between the melting point of compound IV and 200° C., preferably between 120° and 170° C. Examples of a suitable solvent are acetonitrile, dimethylformamide, benzene, toluene or chlorobenzene. Auxiliary bases can be tertiary amines, such as triethylamine, tributylamine, dimethylaniline or pyridine, but also alkali metal hydrides, such as sodium hydride, potassium hydride or lithium hydride, or alkali alcoholates, such as potassium tertbutylate, which form an alkali salt from the compound of Formula IV.

Conversion of the free bases of general Formula I into the pharmacologically compatible acid addition salts according to this invention takes place by reacting the base with the corresponding acid in accordance with standard directives.

Additional details for preparing the compounds of general Formula I can be seen from Synthesis Examples 1-12 set forth below which also contain the production of the respective starting compound of general Formula II. Further compounds of general Formula I such as those listed after Example 12 and starting compounds of general Formula II can be prepared by analogous procedures using the correspondingly adapted reactants.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth in degrees Celsius and unless otherwise indicated, all parts and percentages are by weight.

The entire disclosures of all applications, patents and publications, if any, cited above and below, and of corresponding application Federal Republic of Germany P 39 26 365.7, filed Aug. 4, 1989, are hereby incorporated by reference.

EXAMPLE 1

4-[1-Cyclohexylidene-1-(imidazolyl)methyl]benzonitrile, Hydrochloride (a) 4-[1-(Imidazolyl)methyl]benzonitrile Under cooling, 23.15 g of imidazole in 250 ml of N,N-dimethylformamide is combined in portions with 14.8 g of sodium hydride, 60% in oil, and stirred for 1.5 hours at 25° up to the end of hydrogen release. In two portions, 50 g of 4-(bromomethyl)benzonitrile is added under ice cooling to this solution and the mixture is agitated for 1.5 hours at 25°. For processing, 100 ml of water is added under ice cooling, the mixture is agitated for 0.25 hour, poured into 1.5 l of ethyl acetate, washed neutral with water, washed twice with sodium chloride and water, dried over sodium sulfate, concentrated to dryness under vacuum, and crystallized from acetone/diethyl ether, thus obtaining 33.6 g of 4-[1-(imidazolyl)-methyl]benzonitrile as colorless crystals, mp 102°.

(b) 4-[1-Cyclohexylidene-1-(imidazolyl)-methyl]benzonitrile, Hydrochloride 1.83 g of 4-[1-(imidazolyl)methyl]benzonitrile is dissolved in 50 ml of tetrahydrofuran and combined at −50° with 7.3 ml of 1.5-molar solution of lithium diisopropylamide in tetrahydrofuran; the mixture is stirred for 0.5 hour, further stirred with 1.05 g of cyclohexanone for 1 hour at −60°, and heated to 25°. Then water is added, the mixture is diluted with ethyl acetate, washed neutral with water, dried over sodium sulfate, and concentrated to dryness under vacuum, yielding 2.7 g of crude 4-[1-hydroxycyclohex-1-yl-1-(imidazolyl)-methyl]benzonitrile.

1.8 g of crude 4-[1-hydroxycyclohex-1-yl-1(imidazolyl)methyl]benzonitrile is refluxed in 20 ml of thionyl chloride for 1 hour. Then the mixture is concentrated to dryness under vacuum and chromatographed on silica gel with dichloromethane/methanol, thus obtaining 304 mg of the free base, mp 128°, which is converted with hydrochloric acid into the oily 4-[1-cyclohexylidene-1-(imidazolyl)methyl]benzonitrile, hydrochloride.

EXAMPLE 2

4-[1-Cyclopentylidene-1-(imidazolyl)methyl]benzonitrile 5.0 g of 4-[1-(imidazolyl)methyl]benzonitrile is dissolved in 150 ml of tetrahydrofuran and combined at −50° with 20 ml of 1.5-molar solution of lithium diisopropylamide in tetrahydrofuran, stirred for 0.5 hour at −60°, combined with 2.5 g of cyclopentanone, further stirred for 1 hour, and heated to 25°. Then water is added to the mixture, the latter is diluted with ethyl acetate, washed neutral with water, dried over sodium sulfate, and concentrated to dryness under vacuum, yielding 6.9 g of crude 4-[1-hydroxycyclopent-1-yl-1-(imidazolyl)methyl]benzonitrile.

6.9 g of crude 4-[1-hydroxycyclopent-1-yl-1-(imidazolyl)methyl]benzonitrile is refluxed in 82 ml of thionyl chloride to 0.5 hour. Then the mixture is concentrated to dryness under vacuum, combined with 2N sodium hydroxide solution, extracted with dichloromethane, dried over sodium sulfate, concentrated to dryness under vacuum, and chromatographed on silica gel with hexane/ethyl acetate, thus producing 3.1 g of 4-[1-cyclopentylidene-1(imidazolyl)methyl]benzonitrile as the free base, mp 108–110°.

EXAMPLE 3

4-[1-Cycloheptylidene 1-(imidazolyl)methyl]benzonitrile 10 g of 4-[1-(imidazolyl)methyl]benzonitrile is dissolved in 270 ml of tetrahydrofuran and combined at −50° with 40 ml of 1.5-molar solution of lithium diisopropylamide in tetrahydrofuran, stirred for 0.5 hour at −60°, combined with 6.5 g of cycloheptanone, stirred further for 1 hour, and heated to 25°. Then water is added, the mixture is diluted with ethyl acetate, washed neutral with water, dried over sodium sulfate, and concentrated to dryness under vacuum, thus producing 16 g of crude 4-[1-hydroxyclohept-1-yl-1-(imidazolyl)

At 0°, 10 g of crude 4-[1-hydroxycyclohept-1-yl-1-(imidazolyl)methyl]benzonitrile is dissolved in 100 ml of dichloromethane and stirred with 10 ml of thionyl chloride for 4 hours. Then the mixture is concentrated to dryness under an oil pump vacuum, taken up in 100 ml of dichloromethane, and stirred with 40 ml of triethylamine for 18 hours at 25°. For working up purposes, the mixture is combined with water, extracted twice with dichloromethane, dried over sodium sulfate, concentrated to dryness under vacuum, and chromatographed on silica gel with hexane/ethyl acetate, thus producing 2.03 g of 4-[1-cycloheptylidene-1(imidazolyl)methyl]benzonitrile as the oily, free base.

EXAMPLE 4

4-[2-Adamantylidene-1-(imidazolyl)methyl]benzonitrile 5.0 g of 4-[1-(imidazolyl)methyl]benzonitrile is dissolved in 100 ml of tetrahydrofuran and combined at −50° with 20 ml of 1.5-molar solution of lithium diisopropylamide in tetrahydrofuran, stirred for 0.5 hour at −60°, combined with 4.3 g of 2-adamantanone, further stirred for 1 hour, and heated to 25°. Then water is added, the mixture is extracted three times with ethyl acetate, washed neutral with water, dried over sodium sulfate, and concentrated to dryness under vacuum, thus obtaining 6.66 g of crude 4-[2-hydroxy-adamant-1-yl-1-(imidazolyl)methyl]benzonitrile.

6.66 g of crude 4-[2-hydroxyadamant-1-yl-1(imidazolyl)methyl]benzonitrile is dissolved at 0° in 50 ml of dichloromethane and stirred at 0° with 12.7 ml of thionyl chloride for 1 hour. Then the mixture is concentrated to dryness under vacuum, dissolved in 50 ml of dichloromethane, stirred with 24 ml of triethylamine for 2 hours, diluted with water, extracted four times with ethyl acetate, washed with sodium chloride solution, dried over sodium sulfate, concentrated to dryness under vacuum, and chromatographed on silica gel with dichloromethane/acetone, yielding 1.55 g of 4-[2-adamantylidene-1-(imidazolyl)methyl]benzonitrile as the free base, mp 155°.

EXAMPLE 5

4-[1-Cyclohexylidene-1-(1,2,4-triazolyl)methyl]benzonitrile (a) 4-[1-(1,2,4-Triazolyl)methyl]benzonitrile 23.5 g of 1,2,4-triazole is combined under cooling in 250 ml of N,N-dimethylformamide in incremental portions with 14.15 g of sodium hydride, 60% in oil, and stirred at 25° for 1 hour until hydrogen release has ceased. To this solution is added 50 g of 4-(bromomethyl)benzonitrile in two portions under ice cooling at 5°, and the mixture is stirred for 2 hours at 25°. For working up purposes, 200 ml of water is added under ice cooling, the mixture is stirred for 1 hour, extracted with ethyl acetate, washed neutral with water, dried over sodium sulfate, concentrated to dryness under vacuum, and chromatographed on silica gel with dichloromethane/methanol, yielding 31.73 g of 4-[1-(1,2,4-triazolyl)methyl]benzonitrile as colorless crystals, mp. 72–73°.

(b) 4-[1-Cyclohexylidene-1-(1,2,4-triazolyl)
methyl]benzonitrile 5 g of 4-[1-(1,2,4-triazolyl)methyl]benzonitrile is dissolved in 100 ml of tetrahydrofuran and combined at −50° with 20 ml of 1.5-molar solution of lithium diisopropylamide in tetrahydrofuran, stirred for 0.5 hour, further agitated with 2.9 g of cyclohexanone for 1 hour at −70°, and heated to 25°. Then water is added, the mixture is extracted with ethyl acetate, washed neutral with water, dried over sodium sulfate, and concentrated to dryness under vacuum, thus obtaining 7.24 g of crude 4-[1-hydroxycyclohex-1-yl-1-(1,2,4-triazolyl)methyl]-benzonitrile.

7.24 g of crude 4-[1-hydroxycyclohex-1-yl-1-(1,2,4-triazolyl)methyl]benzonitrile is dissolved at 0° in 50 ml of dichloromethane and stirred for 1 hour at 0° with 22.7 ml of thionyl chloride. Then the mixture is concentrated to dryness under vacuum, dissolved in 50 ml of dichloromethane, stirred with 30 ml of triethylamine for 2 hours, diluted with water, extracted four times with ethyl acetate, washed with sodium chloride solution, dried over sodium sulfate, concentrated to dryness under vacuum, and chromatographed on silica gel with hexane/ethyl acetate, yielding 1.45 g of 4-[1-cyclohexylidene-1-(1,2,4-triazolyl)methyl]benzonitrile as a free base, mp 92–93°.

EXAMPLE 6

4-[1-Cyclopentylidene-1-(1,2,4-triazolyl)methyl]benzonitrile 5 g of 4-[1-(1,2,4-triazolyl)methyl]benzonitrile is dissolved in 100 ml of tetrahydrofuran and combined at −50° with 20 ml of 1.5-molar solution of lithium diisopropylamide in tetrahydrofuran, stirred for 0.5 hour, further stirred for 1 hour with 2.4 g of cyclopentanone at −70°, and heated to 25°. Then water is added, the mixture is extracted twice with ethyl acetate, washed neutral with water, dried over sodium sulfate, and concentrated to dryness under vacuum, thus obtaining 7.21 g of crude 4-[1-hydroxycyclopent-1-yl-1-(1,2,4-triazolyl)methyl]benzonitrile.

7.21 g of crude 4-[1-hydroxycyclopent-1-yl-1-(1,2,4-triazolyl)methyl]benzonitrile is dissolved in 50 ml of dichloromethane at 0° and stirred at 0° with 24 ml of thionyl chloride for 1 hour. Then the mixture is concentrated to dryness under vacuum, dissolved in 50 ml of dichloromethane, stirred for 2 hours with 32 ml of triethylamine, diluted with water, extracted four times with ethyl acetate, washed with sodium chloride solution, dried over sodium sulfate, concentrated to dryness under vacuum, and chromatographed on silica gel with hexane/ethyl acetate, thus obtaining 2.1 g of 4-[1-cyclopentylidene-1-(1,2,4triazolyl)methyl]benzonitrile as the free base, mp 72°.

EXAMPLE 7

4-[1-Cycloheptylidene-1-(1,2,4-triazolyl)methyl]benzonitrile 5 g of 4-[1-(1,2,4-triazoluyl)methyl]benzonitrile is dissolved in 100 ml of tetrahydrofuran and combined at −50° with 19.8 ml of 1.5-molar solution of lithium diisopropylamide in tetrahydrofuran, stirred for 0.5 hour, further stirred for 1 hour at −70°. with 3.05 g of cycloheptanone, and heated to 25°. Then the mixture is combined with water, extracted twice with ethyl acetate, washed neutral with water, dried over sodium sulfate, and concentrated to dryness under vacuum, thus obtaining 7.9 g of crude 4-[1-hydroxycyclohept-1-yl-1-(1,2,4-triazolyl)methyl]benzonitrile.

7 g of crude 4-[1-hydroxycyclohept-1-yl-1-(1,2,4-triazolyl)methyl]benzonitrile is dissolved in 50 ml of dichloromethane at 0° and stirred with 20 ml of thionyl chloride for 1 hour at 0°. Then the mixture is concentrated to dryness under an oil pump vacuum, dissolved in 50 ml of dichloromethane, stirred for 2 hours with 30 ml of triethylamine, diluted with water, extracted three times with ethyl acetate, washed with sodium chloride solution, dried over sodium sulfate, concentrated to dryness under vacuum, and chromatographed on silica gel with hexane/ethyl acetate, thus producing 1.9 g of 4-[1-cycloheptylidene-1-(1,2,4triazolyl)methyl]benzonitrile as the free base, mp 79–80°.

EXAMPLE 8

4-[2-Adamantylidene-1-(1,2,4-triazolyl)methyl]benzonitrile 5 g of 4-[1-(1,2,4-triazolyl)methyl]benzonitrile is dissolved in 100 ml of tetrahydrofuran and combined at −50° with 19.8 ml of 1.5-molar solution of lithium diisopropylamide in tetrahydrofuran, stirred for 0.5 hour, further stirred with 4.25 g of adamantanone for 1 hour at −70°, and heated to 25°. Then water is added, the mixture is extracted twice with ethyl acetate, washed neutral with water, dried over sodium sulfate, and concentrated to dryness under vacuum, yielding 9 g of crude 4-(2-hydroxyadamant-2-yl-1-(1,2,4-triazolyl)methyl]benzonitrile.

9 g of crude 4-[2-hydroxyadamant-2-yl-1-(1,2,4-triazolyl)methyl]benzonitrile is dissolved at 0° in 50 ml of dichloromethane and stirred at 0° with 24 ml of thionyl chloride for 1 hour. Then the mixture is concentrated to dryness in an oil pump vacuum, dissolved in 50 ml of dichloromethane, stirred for 2 hours with 32 ml of triethylamine, diluted with water, extracted three times with ethyl acetate, washed with sodium chloride solution, dried over sodium sulfate, concentrated to dryness under vacuum, and chromatographed on silica gel with hexane/ethyl acetate, yielding 5.3 g of 4-[2-adamantylidene-1-(1,2,4triazolyl)methyl]benzonitrile as the free base, mp 130°, which is converted with hydrochloric acid into the hydrochloride, mp 105°.

EXAMPLE 9

4-[1-Cyclohexylidene-1-(1,2,3-triazolyl)methyl]benzonitrile (a) 4-Azidomethylbenzonitrile 50 g of 4-bromomethylbenzonitrile is dissolved in 350 ml of 1,3-dimethyl-2-imidazolidinone and stirred at 25° for 2 hours with 32.5 g of sodium azide. The mixture is subsequently combined with 500 ml of water under ice cooling, extracted twice with dichloromethane, washed with water, dried over sodium sulfate, concentrated to dryness under vacuum, and chromatographed on silica gel with hexane/ethyl acetate, thus obtaining 39 g of 4-azidomethylbenzonitrile as a colorless liquid.

(b) 4-[1-(1,2,3-Triazolyl)methyl]benzonitrile 38.9 g of 4-azidomethylbenzonitrile is refluxed in 400 ml of toluene with 42 ml of trimethylsilylacetylene for 5 hours at 120°, combined with another 21 ml of trimethylsilylacetylene, and once again refluxed for 3 hours at 120°. Then the mixture is concentrated under vacuum, yielding 63 g of crude 4-[4-trimethylsilyl-(1,2,3-triazol-1-yl)methyl]benzonitrile. The latter is refluxed with a mixture of 700 ml of glacial acetic acid, 380 ml of water, as well as 110 ml of tetrahydrofuran for 2 hours. For working up purposes, the mixture is poured into sodium bicarbonate solution, extracted three times with dichloromethane, washed neutral with water, dried over sodium sulfate, concentrated to dryness under vacuum, and recrystallized from ethyl acetate/hexane, yielding 32.8 g. of 4-[1-(1,2,3-triazolyl)methyl]benzonitrile as colorless crystals, mp 83°.

(c) 4-[1-Cyclohexylidene-1-(1,2,3-triazolyl)-methyl]benzonitrile 5 g of 4-[1-(1,2,3-triazolyl)methyl]benzonitrile is dissolved in 100 ml of tetrahydrofuran and combined at −50° with 20 ml of 1.5-molar solution of lithium diisopropylamide in tetrahydrofuran, stirred for 0.5 hour, further stirred with 2.9 g of cyclohexanone for 1 hour at −70°, and heated to 25°. Then water is added, the mixture is extracted three times with ethyl acetate, washed with water, dried over sodium sulfate, and concentrated to dryness under vacuum, thus obtaining 7.6 g of crude 4-[1-hydroxycyclohex-1-yl-1-(1,2,3-triazolyl)methyl]benzonitrile.

7.6 g of crude 4-[1-hydroxycyclohex-1-yl-1-(1,2,3-triazolyl)methyl]benzonitrile is dissolved at 0° in 50 ml of dichloromethane and stirred at 0° for 1 hour with 22.7 ml of thionyl chloride. Then the mixture is concentrated to dryness under vacuum, dissolved in 50 ml of dichloromethane, stirred with 30 ml of triethylamine for 2 hours, diluted with water, extracted three times with ethyl acetate, washed with water, dried over sodium sulfate, concentrated to dryness under vacuum, and chromatographed on silica gel with hexane/ethyl acetate, thus obtaining 2.6 g of 4-[1-cyclohexylidene-1-(1,2,3-triazolyl)methyl]benzonitrile as the free base. 132–133° C.

EXAMPLE 10

4-[1-Cyclopentylidene-1-(1,2,3-triazolyl)methyl]benzonitrile 5 g of 4-[1-(1,2,3-triazolyl)methyl]benzonitrile is dissolved in 100 ml of tetrahydrofuran and combined at −60° with 20 ml of 1.5-molar solution of lithium diisopropylamide in tetrahydrofuran, stirred for 0.5 hour, further stirred for 1 hour at −70° with 2.4 g of cyclopentanone, and heated to 25°. Then the mixture is combined with water, extracted three times with ethyl acetate, washed with water, dried over sodium sulfate, and concentrated to dryness under vacuum, thus obtaining 7.1 g of crude 4-[1-hydroxycyclopent-1-yl-1-(1,2,3-triazolyl)methyl]benzonitrile.

7.1 g of crude 4-[1-hydroxycyclopent-1-yl-1-(1,2,3-triazolyl)methyl]benzonitrile is dissolved at 0° in 50 ml of dichloromethane and stirred with 24 ml of thionyl chloride for 1 hour at 0°. Then the mixture is concentrated to dryness under vacuum, dissolved in 50 ml of dichloromethane, stirred with 32 ml of triethylamine for 2 hours, diluted with water, extracted three times with ethyl acetate, washed with water, dried over sodium sulfate, concentrated to dryness under vacuum, and chromatographed on silica gel with hexane/ethyl acetate, yielding 2.1 g of 4-[1-cyclo-pentylidene-1-(1,2,3-triazolyl)methyl]benzonitrile as the free base, 108–109°.

EXAMPLE 11

5-(Cyclohexylidene-1-imidazolylmethyl)thiophene-2-carbonitrile (a) 1-(5-Bromo-2-thienylmethyl)imidazole 20 g of 5-bromothiophene-2-carbaldehyde is reduced with 4 g of sodium borohydride in 100 ml of 2-propanol in the usual way to 20 g of 5-bromo-2-thiophene methanol. The latter is dissolved with 30 ml of dichloromethane and stirred with 25 ml of thionyl chloride at 25° for 2 hours. After evaporation under vacuum and redistilling twice with toluene, the residue is dissolved in 15 ml of dimethylformamide and added to a solution of imidazole sodium prepared from 7.14 g of imidazole and 3.15 9 of a sodium hydride-oil suspension (85%) in 30 ml of dimethylformamide. After 20 hours at 25°, the mixture is poured on 2N hydrochloric acid and extracted with ether. The aqueous phase is made alkaline with potassium carbonate and extracted with ethyl acetate, the organic phase is washed with water, dried over sodium sulfate, concentrated under vacuum, and distilled with the use of a bulb tube, thus obtaining 17.3 g of 1-(5-bromo-2thienylmethyl)imidazole, bp 170° at 0.03 mbar.

(b) 5-(1-Imidazolylmethyl)thiophene-2-carbonitrile 10 g of 1-(5-bromo-2-thienylmethyl)-imidazole is refluxed with 10 g of copper(I) cyanide in 150 ml of dimethylformamide for 20 hours. Then the mixture is poured on water, the crystals are suctioned off and stirred with 200 ml of 25% ammonia water for 1 hour at room temperature. The mixture is then extracted with ethyl acetate, washed with water, dried over sodium sulfate, concentrated under vacuum, and distilled, using a bulb tube. Yield: 6.2 g of 5-(1-dazolylmethyl)thiophene-2-carbonitrile as orange-colored crystals, mp 73–75°.

(c) 5-(Cyclohexylidene-1-imidazolylmethyl)-thiophene-2-carbonitrile 1.8 g of 5-(1-imidazolylmethyl)thiophene-2-carbonitrile is combined in 30 ml of tetrahydrofuran at −50° with 7.3 ml of a 1.5-molar solution of lithium diisopropylamide in tetrahydrofuran and further stirred for 0.5 hour. Subsequently, 1.05 g of cyclohexanone is added dropwise at −70°, the mixture is stirred at −70° for 1 hour, and then gradually warmed up to 25°. For working up purposes, the reaction mixture is poured on water, extracted with ethyl acetate, the organic phase is extracted with 2N hydrochloric acid, adjusted to alkaline with potassium carbonate, again extracted with ethyl acetate, dried over sodium sulfate, and concentrated to dryness under vacuum, thus producing crude 5-[hydroxy-(1-imidazolyl)methyl]thiophene-2-carbonitrile as a foam. This foam is stirred in 10 ml of dichloromethane at 0° with 5 ml of thionyl chloride for 1 hour, concentrated to dryness under an oil pump vacuum, and stirred with 7 ml of triethylamine for 20 hours at 25°. Then the mixture is poured on water, extracted with ethyl acetate, washed with water, dried over sodium sulfate, concentrated under vacuum, and chromatographed on silica gel with dichloromethane/isopropanol, thus producing 180 mg of 5-(cyclohexylidene-1-imidazolylmethyl)thiophene-2-carbonitrile as a yellow oil, in addition to a small amount of 5-[(1-cyclohexenyl)-(1-imidazolyl)methyl]thiophene-2-carbonitrile.

EXAMPLE 12

5-[Cyclopentylidene-(1-imidazolyl)methyl]thiophene-2-carbonitrile (a) Analogously to Example 11, a crude product is obtained from 1.8 g of 5-(1-imidazolylmethyl)-thiophene-2-carbonitrile and 0.93 ml of cyclopentanone. This crude product is distilled on a bulb tube at 230°/0.03 mbar. After crystallization from ether, 120 mg of the title compound is obtained from the distillate in the form of colorless crystals, mp 90–92°.

(b) (1) 5-Cyclopentylidenemethylthiophene-2-carbonitrile 8 g of 5-bromomethylthiophene-2-carbonitrile (prepared by brominating 5.7 g of 5-methylthiophene-2-carbonitrile and 8.42 g of N-bromosuccinimide in 68 ml of carbon tetrachloride under exposure to light and with the addition of 185 mg of benzoyl peroxide) is refluxed for 30 minutes in 35 ml of chloroform with 5.6 g of hexamethylenetetramine. The precipitated salt is suctioned off and refluxed in 30 ml of acetic acid and 30 ml of water for 2 hours. After extraction with ether, washing of the ether phase with water, drying, and evaporation, 2.43 g of 5-cyanothiophene-2-aldehyde is obtained.

The corresponding phosphorane is produced from 3 g of cyclohexyltriphenylphosphonium bromide in 80 ml of ether by dropwise addition of 4.5 ml of a 1.5-molar solution of butyllithium in hexane at room temperature. To this product is added dropwise 1 g of 5-cyanothiophene-2-aldehyde in 45 ml of ether. After 16 hours of agitation at room temperature, a precipitate is suctioned off, and the filtrate is concentrated by evaporation. The residue is recrystallized from isopropanol, thus obtaining 610 mg of the title compound (b) (1), mp 98–100°.

In a second process, 20 g of 5-bromomethyl-thiophene-2-carbonitrile is heated with 200 ml of triethyl phosphite for 4 hours to 150°. Then triethyl phosphite is removed at 40°–60°/0.06 mbar, and the residue is distilled on a bulb tube at 130°–150°/0.004 mbar, resulting in 24 g of (5-cyano-2-thienyl)methylphosphonic acid diethyl ester. Of this product, 5 g is added dropwise, with 1.5 ml of cyclopentanone in 5 ml of tetrahydrofuran, to a suspension of 581 mg of sodium hydride/oil (80% strength) and 116 mg of 15-crown-5 in 5 ml of tetrahydrofuran. After 2 hours of agitation at room temperature, the mixture is poured on water and extracted with ethyl acetate. The ethyl acetate phase is dried and evaporated, and the residue is recrystallized from isopropanol, thus obtaining 3.0 g of 5-cyclopentylidenemethylthiophene-2-carbonitrile, identical to the product described above.

(2) 3 g of 5-cyclopentylidenemethyl-thiophene-2-carbonitrile is dissolved in 30 ml of dichloromethane and combined with 31 ml of a 0.5-molar solution of bromine in dichloromethane. After 3 hours of stirring at room temperature, the mixture is diluted with ethyl acetate, shaken with dilute sodium thiosulfate solution, dried, and evaporated. The residue is maintained with 13 g of imidazole for 12 hours under argon at 120°, then poured on 2-molar hydrochloric acid, and extracted with ether. The aqueous phase is alkalinized with potassium carbonate and extracted with ethyl acetate. After washing the ethyl acetate phase with water, drying, and evaporation, a crude product is obtained which is chromatographed over 250 g of silica gel with dichloromethane/isopropanol (100:0 to 97:3). Thereafter the mixture is crystallized from ether, thus obtaining 70 mg of 5-[cyclopentylidene-(1-imidazolyl)methyl]thiophene-2-carbonitrile, identical to the material described in (a).

Analogously to the above directions, further compounds of Formula I according to this invention were produced, namely:

4-[1-(3,3,5,5-tetramethyl-1-cyclohexylidene)-1(1-imidazolyl)methyl]benzonitrile; mp: 111–113° C.;

4-[1-cycloheptylidene-1-(1,2,3-triazol-1-yl)methyl]benzonitrile; mp: 91°–93° C.;

4-[1-cyclodecylidene-1-(1-imidazolyl)methyl]benzonitrile; oil;

4-[1-cycloheptylidene-1-(1-imidazolyl)methyl]benzonitrile, hydrochloride; oil;

4-[1-(4-tert-butyl-1-cyclohexylidene)-1-(1-imidazolyl)-methyl]benzonitrile; oil;

4-[1-(3,4-dimethyl-1-cyclopentylidene)-1-(1-imidazolyl)methyl]benzonitrile; (mixture of isomers cis/trans); oil;

4-[1-(3,5-dimethyl-1-cyclohexylidene)-1-(1-imidazolyl)-methyl]benzonitrile; oil;

4-[1-(4-methyl-1-cyclohexylidene)-1-(1-imidazolyl)methyl]benzonitrile; mp: 85°–87° C.;

4-[1-cyclononylidene 1-(1-imidazolyl)methyl]benzonitrile; oil;

4-[1-(bicyclo[3.3.1]non-9-ylidene)-1-(1-imidazolyl)methyl]benzonitrile; mp: 138°–139° C.;

4-[1-(1-imidazolyl)-1-(spiro[5.5]undec-3-ylidene)methyl]benzonitrile; oil;

4-[1-cyclooctylidene 1-(1-imidazolyl)methyl]benzonitrile; mp: 111-112 C;

4-[1-(2,6-dimethyl-1-cyclohexylidene)-1-(1-imidazolyl)-methyl]benzonitrile; oil;

4-[1-cyclohexylidene-1-(1-imidazolyl)methyl]benzonitrile; mp: 128° C.;

4-[1-(2-adamantylidene)-1-(1,2,3-triazol-1-yl)methyl]-benzonitrile; mp: 151°–153° C.;

4-[1-(2-adamantylidene)-1-(1,2,4-triazol-1-yl)methyl]-benzonitrile; mp: 105° C.;

4-[1-(2-adamantylidene)1-(1-imidazolyl)methyl]benzonitrile, hydrochloride; foam;

4-[1-cyclobutylidene 1-(1-imidazolyl)methyl]benzonitrile; mp: 120°–122° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cycloalkylene azole of formula I

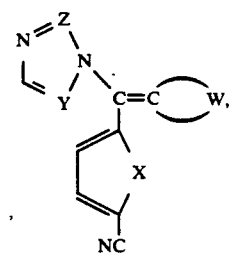

wherein

is a cycloalkylidene group of from 4–20 carbon atoms or a polycycloalkylidene group of from 7–20 carbon atoms optionally carrying one of more alkyl substituents;

X is the grouping

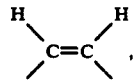

an oxygen or sulfur atom; and

Y is

and Z is a nitrogen atom, or a pharmaceutically compatible salt of a cycloalkylene azole of Formula I with acid.

2. A cycloalkylene azole according to claim 1, where

is a cyclopentylidene, cyclohexylidene or cycloheptylidene group.

3. A cycloalkylene azole according to claim 1, where

is a cyclobutylidene, cyclooctylidene, cyclononylidene, cyclodecylidene group.

4. A cycloalkylene azole according to claim 1, where

is a is a 2-adamantylidene group.

5. A cycloalkylene azole according to claim 1, where

is a bicyclo[3.3.1]non-9-ylidene or spiro[5.5]undec-3-ylidene group.

6. A cycloalkylene azole according to claim 1, where

is a group with at least one straight-chain or branched $C_{1-6}$-alkyl substituent.

7. A cycloalkylene azole according to claim 1, where X is the grouping

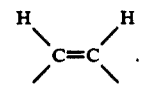

8. A cycloalkylene azole according to claim 1, where X is a sulfur atom.

9. The compounds:
4-[1-cyclohexylidene-1-(1,2,3-triazolyl)methyl]benzonitrile;
4-[1-cyclohexylidene-1-(1,2,3-triazolyl)methyl]benzonitrile;
4-[1-(2-adamantylidene)-1-(1,2,3-triazol-1-yl)methyl]-benzonitrile;
and their pharmaceutically compatible salts with acids.

10. A cycloalkylene azole of claim 1, wherein the cycloalkylidene groups or polycycloalkylidene groups are substituted with 1–4 straight-chain or branched alkyl groups of 1–6 carbon atoms.

11. A pharmaceutical composition which comprises an effective amount of a compound of claim 1 and a pharmaceutically compatible vehicle.

12. A method for the treatment of a disease caused or dependent on estrogens, comprising administering to a host an effective amount of a compound of claim 1.

13. A method for inhibiting aromatase activity in a host which comprises administering to said host an effective amount of a compound of claim 1.

14. A method for the treatment of estrogen-induced or stimulated tumors which comprises administering to a host an effective amount of a compound of claim 1.

15. A method for the treatment of mamma carcinoma or prostate hyperplasia comprising administering to a host an effective amount of in need of such treatment a compound of claim 1.

* * * * *